(12) United States Patent
Miljkovic et al.

(10) Patent No.: US 7,320,806 B2
(45) Date of Patent: Jan. 22, 2008

(54) COMPOSITIONS AND METHODS FOR TREATING NIDDM AND OTHER CONDITIONS AND DISORDERS ASSOCIATED WITH AMPK REGULATION

(75) Inventors: Dusan Miljkovic, San Diego, CA (US); Zbigniew Pietrzkowski, San Diego, CA (US)

(73) Assignee: VDF Futureceuticals, Inc., Momence, IL (US)

( * ) Notice: Subject to any disclaimer, the term of this patent is extended or adjusted under 35 U.S.C. 154(b) by 104 days.

(21) Appl. No.: 10/526,837

(22) PCT Filed: Aug. 29, 2003

(86) PCT No.: PCT/US03/27012

§ 371 (c)(1),
(2), (4) Date: Oct. 26, 2005

(87) PCT Pub. No.: WO2004/021980

PCT Pub. Date: Mar. 18, 2004

(65) Prior Publication Data

US 2006/0134240 A1    Jun. 22, 2006

(51) Int. Cl.
*A61K 36/8998* (2006.01)
(52) U.S. Cl. .................................... 424/750
(58) Field of Classification Search ............ None
See application file for complete search history.

(56) References Cited

U.S. PATENT DOCUMENTS

| 4,797,421 | A | 1/1989 | Ariga et al. |
| 5,591,772 | A | 1/1997 | Lane et al. |
| 6,270,774 | B1 * | 8/2001 | Hsia et al. ............. 424/195.11 |
| 6,365,176 | B1 | 4/2002 | Bell et al. |

OTHER PUBLICATIONS

1997. Merrill et al. AICA ribose increases AMP-activated protein kinase fatty acid oxidation, and glucose uptake in rat muscle. American Journal of Physiology. Dec.; 273 (6) pp. 1107-1112.*
1991. Hejgaard et al. Two antifungal thaumatin-like proteins from barley grain. FEBS. vol. 291, No. 1, pp. 127-131.*
1985. Kannel. Lipids, diabetes, and coronary heart disease: insights from the Framingham study. Am. Heart Jour. Nov.; 110 (5) Abstract.*
Derwent, Acc-No. 1999-169889, Asahi Beer Malt KK. "Wheat or barley malt based snack foods—makes use of germinated wheat or barley malt which is roasted and starch is gelantinised." AJP-11018707A, Jan. 26, 1999, see Abstract.

* cited by examiner

*Primary Examiner*—Christopher R. Tate
*Assistant Examiner*—Melenie McCormick
(74) *Attorney, Agent, or Firm*—Fish & Associates, PC

(57) ABSTRACT

Compositions and methods are provided to increase glucose uptake in a cell as well as to treat a patient suffering from a condition or disorder associated with AMPK regulation. Particularly contemplated compositions include a compound that is isolated from a plant that has AICAR-like activity. In another aspect of the invention, contemplated compositions comprise a non-insulin compound that has AICAR-like activity and activates AMPK in a cell.

12 Claims, 13 Drawing Sheets

```
                    ┌─ 100
                    ↓

110 ─┐  ┌─────────────────────────────────────┐
     └──│ Providing a composition that includes a │
        │ compound that binds to a thaumatin-like │
        │              protein                    │
        └─────────────────────────────────────┘
                         │
                         ↓
120 ─┐  ┌─────────────────────────────────────┐
     └──│ Administering the composition to an    │
        │ organism in a dosage effective to decrease │
        │     the concentration of glucose        │
        └─────────────────────────────────────┘
```

Figure 1

| Group | No. of Patients | Before treatment | | After treatment | | Decrease (%) |
|---|---|---|---|---|---|---|
| | | range | mean | range | mean | |
| Plasma Glucose (mMol/L) | | | | | | |
| I | 6 | 6.8-8.5 | 7.6 | 6.8-7.7 | 7.2 | 5.6 |
| II | 8 | 8.1-10.2 | 9.0 | 7.0-9.0 | 7.3 | 23.3 |
| III | 7 | 11.6-14.7 | 12.5 | 6.0-10.2 | 8.1 | 54.3 |
| Glucosylated Hemoglobin-HbA1c(%) | | | | | | |
| I | 7 | 8.0-10.0 | 9.1 | 7.6-9.0 | 8.0 | 13.8 |
| II | 8 | 10.1-19.6 | 13.0 | 6.5-10.0 | 8.1 | 60.5 |

Figure 4A

| Patient | 0 days | | 15 days | | 30 days | | 45 days | | 60 days | | 75 days | | 90 days | |
|---|---|---|---|---|---|---|---|---|---|---|---|---|---|---|
| | F | PP | F | PP | F | PP | F | PP | F | PP | F | PP | F | PP |
| 1 | 10.9 | 11.5 | 8.6 | 9.9 | 9.8 | 9.9 | 7.5 | 13.4 | 9.1 | 9.5 | 8.9 | 10.2 | 8.8 | 12.7 |
| 2 | 7.2 | 9.9 | 5.8 | 6.8 | 6.3 | 8.3 | 5.4 | 6.0 | 5.9 | 7.8 | 5.7 | 6.2 | 5.4 | 5.8 |
| 3 | 11.0 | 18.0 | 10.6 | 13.3 | 9.2 | 11.9 | 10.9 | 13.5 | 10.3 | 12.6 | 9.1 | 11.1 | 10.0 | 10.7 |
| 4 | 5.7 | 8.2 | 5.9 | 9.3 | 6.5 | 7.5 | 6.4 | 6.6 | 5.8 | 6.4 | 5.6 | 5.9 | 5.4 | 6.2 |
| 5 | 5.9 | 7.3 | 3.9 | 5.1 | 5.3 | 6.1 | 5.3 | 7.9 | 5.6 | 5.9 | 5.6 | 5.9 | 5.0 | 5.5 |
| 6 | 7.5 | 10.7 | 5.3 | 9.8 | 6.4 | 6.8 | 5.0 | 10.0 | 5.1 | 9.0 | 4.7 | 6.1 | 4.2 | 6.2 |
| 7 | 6.5 | 8.8 | 6.6 | 8.8 | 6.5 | 7.8 | 6.8 | 6.9 | 6.6 | 8.5 | 6.3 | 6.5 | 5.6 | 6.3 |
| 8 | 10.8 | 17.0 | 10.9 | 19.4 | 12.2 | 18.1 | 10.0 | 15.6 | 11.8 | 18.1 | 13.0 | 22.4 | 10.0 | 16.5 |
| 9 | 14.4 | 16.6 | 11.8 | 16.7 | 14.4 | 18.6 | 11.0 | 15.2 | 12.6 | 18.2 | 10.5 | 16.4 | 10.0 | 14.3 |
| 10 | 9.9 | 13.2 | 8.1 | 11.2 | 8.2 | 12.0 | 7.9 | 10.2 | 7.5 | 9.8 | 7.3 | 9.5 | 7.0 | 8.2 |

Figure 4B

| No. of patients | Before treatment | | After treatment | |
|---|---|---|---|---|
| | range | mean | range | mean |
| Triglycerides (mMol/L) | | | | |
| 8 | 3.6-17.2 | 8.4 | 1.1-10.3 | 4.2 |
| TG/HDL | | | | |
| 12 | 3.7-11.7 | 6.4 | 3.0-9.4 | 5.2 |
| LDL/HDL | | | | |
| 8 | 0.8-4.3 | 2.2 | 0.65-3.1 | 1.5 |

Figure 5A

| | Triglycerides | | Cholesterol | | LDL/Cholesterol | | HDL/Cholesterol | |
|---|---|---|---|---|---|---|---|---|
| | Before | After | Before | After | Before | After | Before | After |
| 1. | 3.2 | 1.3 | 8.5 | 6.8 | 5.7 | 3.0 | 0.7 | 1.2 |
| 2. | 1.3 | 1.3 | 7.1 | 7.7 | 5.3 | 5.7 | 1.2 | 1.4 |
| 3. | 2.6 | 1.9 | 8.4 | 8.9 | 5.7 | 5.4 | 1.4 | 1.7 |
| 4. | 2.4 | 2.2 | 5.9 | 5.1 | 3.5 | 3.2 | 1.1 | 1.3 |
| 5. | 2.1 | 3.4 | 6.0 | 4.5 | 3.2 | 3.1 | 1.1 | 1.3 |
| 6. | 1.1 | 1.3 | 6.5 | 6.5 | 3.7 | 3.8 | 1.1 | 1.2 |
| 7. | 2.5 | 2.7 | 5.4 | 6.3 | 4.3 | 4.1 | 0.9 | 1.0 |
| 8. | 2.1 | 2.0 | 7.6 | 7.2 | 4.9 | 4.6 | 1.7 | 1.8 |
| 9. | 5.8 | 5.2 | 6.8 | 6.5 | 5.1 | 5.2 | 0.9 | 1.0 |
| 10. | 1.2 | 1.2 | 5.2 | 5.4 | 3.8 | 3.5 | 0.9 | 1.2 |

Figure 5B

Intermediate activities by hours in % compared to control

| Sample | 1st hour | 2nd | 3rd | 4th | 5th | 6th |
|---|---|---|---|---|---|---|
| Retentate | 5.7 | 30.7 | 41.2 | 51.5 | 64.7 | 65.8 |
| Permeate | 76.3 | 39.1 | 34.7 | 48.5 | 53.8 | nd |

COMPOSITIONS AND METHODS FOR TREATING NIDDM AND OTHER CONDITIONS AND DISORDERS ASSOCIATED WITH AMPK REGULATION

The present application relates to, and incorporates by reference each in their entirety, the following previously filed international applications: PCT/US01/07527 filed on Mar. 8, 2001 and PCT/US02/07199, filed Mar. 8, 2002.

FIELD OF THE INVENTION

The field of the invention relates to dietary supplements and pharmaceutical compositions as well as related methods.

BACKGROUND OF THE INVENTION

Elevated blood glucose and blood lipids are a relatively common underlying condition in numerous diseases and may be acquired in various ways. Among other causes, elevated blood glucose levels are frequently precipitated by an altered metabolism associated with a diabetic condition, and treatment of diabetic conditions often includes insulin therapy along with synthetic oral anti-diabetic agents, such as metformin, sulfonylurea, etc. Despite an improvement of some clinical parameters (i.e. reduction of blood glucose to at least some extent) in people with elevated blood lipid and blood glucose, various side effects, including insulin resistance, allergic reactions, etc. may arise from long-term treatment using insulin.

Alternative treatments of diabetes, and especially non-insulin dependent diabetes mellitus (NIDDM), are frequently based on yeast, or derivatives of yeast. Yeast can be grown in the presence of chromium salts, and yeast cells or extracts of cells grown in that manner are particularly rich in "glucose tolerance factor" (GTF), a compound known to enhance the biological effect of insulin. Although some yeast preparations help reduce elevated blood glucose concentrations, in many cases, considerable amounts of yeast preparations must be ingested for a substantial period in order to improve a hyperglycemic condition. Moreover, long-term use of yeast preparations over extended periods tends to become problematic for some patients, especially in patients who have a history of yeast infections. Still further, many crude yeast preparations have a bitter taste that some patients may find objectionable.

To alleviate at least some of the problems associated with yeast preparations, concentrated, de-bittered and freeze dried yeast preparations have been developed. Such preparations are typically in tablet form, and may conveniently be ingested during a meal. However, the relatively high degree of processing of such cells/extracts may reduce the biological potency of the yeast preparation. Moreover, preservatives and additives (e.g., for pressing or otherwise forming of tablets) are typically needed to maintain at least some anti-hyperglycemic activity.

In still other methods of reducing blood glucose on a non-insulin basis, chromium picolinate may be administered. Chromium picolinate is reported to be moderately effective in reducing an elevated blood glucose level in human. However, chromium picolinate exhibits considerable toxicity and may therefore not be generally regarded as safe.

It has recently been reported that methods to increase intracellular levels of activated AMPK result in one of a number of beneficial effects, including reducing insulin resistance and glucose concentrations in an organism. However, although various methods to increase intracellular levels of activated AMPK are known in the art, all or almost all of them suffer from one or more disadvantages. Therefore, there is still a need to provide improved compositions and methods to increase intracellular levels of activated AMPK.

SUMMARY OF THE INVENTION

The present invention is directed to compositions and methods to increase intracellular levels of activated AMPK, which results in one of a number of beneficial effects in an organism.

In one aspect of the inventive subject matter, a composition is isolated from a plant or from a malted seed thereof, has AICAR-like activity, and increases glucose uptake into a cell. The composition is preferred to be insulin independent. The composition is also preferred to comprise a compound that activates adenosine 5'-monophosphate-activated protein kinase (AMPK), where the compound preferably has a molecular weight (Mw) of no more than 2000 and a UV light absorption maximum at about 260 nm. It is further preferred that the composition is present in a medium surrounding the cell at a concentration of between about 2-10 micrograms per milliliter, and that the medium surrounding the cell is depleted of at least one of a nutrient and oxygen. The cell is contemplated to be a myocyte or part of an in vivo tissue such as liver tissue, skeletal muscle tissue, pancreatic tissue, or adipose tissue.

In another aspect of the inventive subject matter, a compound is identical with a molecule isolated from *Hordeum vulgare* or from a malted seed thereof, and has AICAR-like activity, increases glucose uptake into a cell, and the molecule isolated from *Hordeum vulgare* reduces blood glucose in an organism when the molecule is administered at a concentration effective to reduce the concentration of glucose. It is preferred that the compound is synthesized in vitro and is modified to increase or decrease at least one of the following: an increase in glucose uptake into a cell; solubility in a solvent; chemical stability; and in vivo specificity.

In a third aspect of the inventive subject matter, a compound is a non-insulin compound that has AICAR-like activity and activates adenosine 5'-monophosphate-activated protein kinase (AMPK) in a cell. It is preferred that the compound is isolated from a *Hordeum vulgare* plant seed, or a malted *Hordeum vulgare* plant seed. It is also preferred that the compound increases glucose uptake in a non-insulin dependent manner when the compound is present in a medium surrounding the cell at a concentration of between 2-10 micrograms per milliliter. It is further preferred that the increase in glucose uptake is reduced when the medium includes L-N-mono-methyl-L-arginine at a concentration of 300 micromoles per liter.

An additional aspect of the inventive subject matter involves the effects that addition of the contemplated compound imparts on a fermentation reaction. In a preferred embodiment of the invention, the contemplated product may be added to fermentation media to increase the rate of fermentation in a fermentation reaction employed to produce a commercial product.

In a further aspect of the inventive subject matter, a method of treating a cell is contemplated to include the steps of identifying the cell as having a condition that activates AMPK and presenting the cell with a compound having AICAR-like activity at a concentration effective to modulate at least one of an import, export, or synthesis of a molecule.

Among the aspects of the inventive subject matter is a process whereby exposing an organism to a composition comprising the contemplated compound results in increased intracellular levels of activated AMPK. In a preferred embodiment of such a process, the import, export or synthesis of a molecule is modulated in response to the increased intracellular levels of activated AMPK that result from exposing the organism to the composition. In one embodiment, the organism is a tissue or cell isolated from a whole organism. In another embodiment, the organism is a whole organism and the process comprises administering the composition to the whole organism to increase intracellular levels of activated AMPK. In a preferred embodiment, the organism is a whole human organism or is a tissue or cell isolated therefrom. An oocyte is one example of a preferred organism that may be employed in a preferred process, where oocyte activity increases in response to the increased intracellular levels of activated AMPK that results from exposing the organism to the composition.

Various objects, features, aspects and advantages of the present invention will become more apparent from the following detailed description of preferred embodiments of the invention.

BRIEF DESCRIPTION OF THE DRAWING

FIG. 1 is a flow diagram showing an exemplary method of reducing blood concentration of glucose according to the inventive subject matter.

FIG. 4A is a table depicting reduction of blood glucose concentrations in human volunteers using contemplated compositions according to the inventive subject matter.

FIG. 4B is another table depicting reduction of blood glucose concentrations in human volunteers using contemplated compositions according to the inventive subject matter.

FIG. 5A is a table depicting reduction of blood lipid concentrations in human volunteers using contemplated compositions according to the inventive subject matter.

FIG. 5B is another table depicting reduction of blood lipid concentrations in human volunteers using contemplated compositions according to the inventive subject matter.

DETAILED DESCRIPTION

Figure 2:
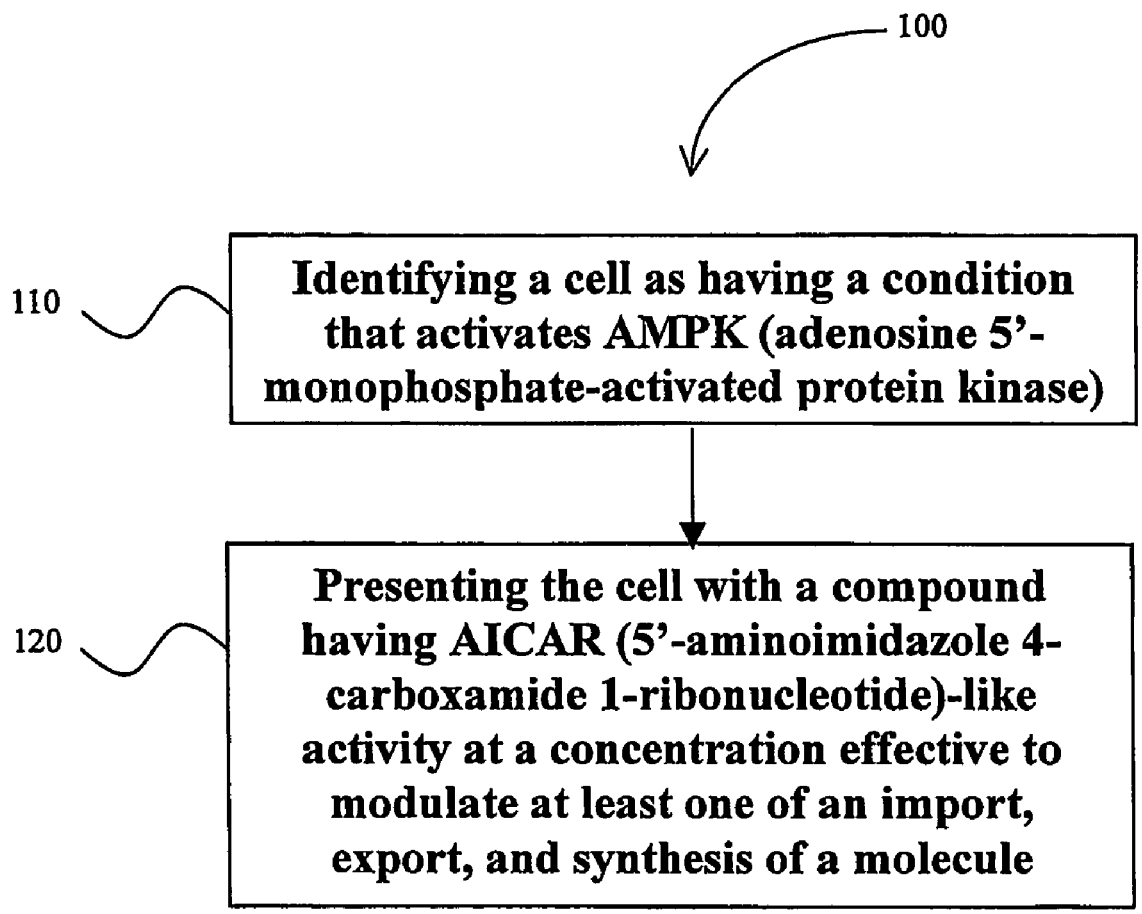
FIG. 2 is a flow diagram showing an exemplary method of treating a cell according to the inventive subject matter.

While not wishing to be bound by theory, applicants believe a mechanism involving the activation of AMPK underlies the reduction in blood glucose that follows administering to an organism a composition comprising a contemplated compound or mixture of compounds. Moreover, recent data collected in several laboratories indicate that AMPK plays a key role in regulation of carbohydrate and fat metabolism, serving as "a metabolic master switch" in response to alterations in cellular energy charge. (Winder et al, Am J Physiol, 2777: E1-10, 1999, herein incorporated by reference in its entirety; Winder, J Appl Physiol, 91:1017-1028, 2001, herein incorporated by reference in its entirety). For example, AMPK phosphorylates numerous target proteins at serine residues in the context of a characteristic sequence recognition motif, and the resulting phosphorylation, in turn, may increase or decrease the rate of the metabolic pathway in which the protein target plays a regulatory role. One form of AMPK is expressed in the cell nucleus, and recent evidence suggests that AMPK can also influence metabolism by regulating gene expression. As such, the utility of the inventive subject matter additionally extends to methods for treating a variety of disorders that are ameliorated through activation of AMPK, as exemplified in the instant application.

As used herein the term "a compound that activates adenosine 5'-monophosphate-activated protein kinase (AMPK)" refers to any compound or mixture of compounds that, when placed in contact with an appropriate cell or organism, increases the rate at which AMPK phophorylates any one of its numerous protein targets. (Winder et al, Am J Physiol, 2777: E1-10, 1999, herein incorporated by reference in its entirety) The term is not limited by the mechanism underlying how the rate at which AMPK phophorylates any one of its numerous protein targets is increased rate. The potential mechanisms through which such a compound may act include, but are not limited to, allosteric mechanisms that affect, directly or indirectly, AMPK activity, as well as mechanisms that act, directly or indirectly, to promote the phosphorylation of the AMPK catalytic subunit catalyzed by a distinct upstream kinase, AMPK kinase (AMPKK).

In FIG. 1, a method 100 of reducing a glucose concentration in an organism has a step 110 in which a composition is provided that includes a compound that binds to a thaumatin-like protein. In a subsequent step 120, the composition is administered to the mammal in a dosage effective to decrease the blood concentration of glucose.

As used herein the term "compound that binds to a thaumatin-like protein" refers to any compound or mixture of compounds that exhibit a binding preference to a thaumatin-like protein from barley of at least 10-fold, more preferably at least 100-fold over binding to other barley proteins, wherein binding of contemplated compounds to the thaumatin-like protein will preferably have a $K_D$ of less than $10^{-3}M$, more preferably of less than $10^{-4}M$. The mode of binding need not be limited to a single interaction (e.g., hydrophobic interaction), but may include multiple interactions (e.g., electrostatic interactions and hydrogen bonding, etc.). It is especially contemplated that binding is reversible, however, irreversible binding is not excluded. Although thaumatin-like proteins from barley are generally preferred binding partners for compounds according to the inventive subject matter, thaumatin-like proteins from alternative sources, including microorganisms, plants, and animals are also contemplated. Thaumatin-like proteins are a well characterized class of polypeptides and are described, for example, in Cvetkovic et al., J. Serb Chem. Soc. 62(9):777-786 (1997), Cvetkovic et al., J. Serb. Chem. Soc. 62(1):51-56 (1997) and Cvetkovic et al., J. Inst. Brew. 103:183-186 (1997), all of which are incorporated by reference herein.

As also used herein, the term "elevated glucose concentration" refers to a concentration that is above the clinical range considered normal (i.e., above 110 mg/dl). Similarly, the term "elevated lipid concentration" refers to a concentration of blood lipids that is above the clinical range considered normal.

In FIG. 2, a method 100 of treating a cell has a step 110 in which the cell has a condition that activates an AMPK (adenosine 5'-monophosphate-activated protein kinase). In a subsequent step 120, the cell is presented with a compound having AICAR-like activity at a concentration effective to modulate at least one of an import, export, and synthesis of a molecule.

The term AICAR refers to 5'-aminoimidazole 4-carboxamide 1-ribonucleotide. As used herein, the terms "AICAR-like activity" and "5'-aminoimidazole 4-carboxamide 1-ribonucleotide" refer to any activity that stimulates insulin independent glucose uptake into L-6 muscle cells that is inhibited by L-NMMA, and which does not include AICA or AICAR or glucose. Also, contemplated compounds do not include tocol or tocotriene compounds. As used herein, the term "L-NMMA" refers to NG-methyl-L-arginine, acetate salt, which is an inhibitor of nitric oxide synthase (NOS). AMPK has known metabolic regulatory effects on fatty acid and carbohydrate metabolism in liver, adipose tissue, pancreatic beta-cells, and skeletal muscle. AMPK is known to effect increases in glucose uptake and increases in fatty acid oxidation in skeletal muscle, increases in fatty acid oxidation, decreases in cholesterol synthesis, and decreases in lipogenesis in the liver. Furthermore, AMPK is known to modulate insulin secretion in pancreatic islets.

It is contemplated that the composition is a pharmaceutical or nutraceutical for treatment of diabetes. In a preferred aspect of the inventive subject matter, the composition is prepared from Hordeum vulgare (as outlined in examples, infra), and orally administered in 3 daily doses of 500 mg, respectively, to a human diagnosed with non-insulin dependent diabetes mellitus (NIDDM). Thus, especially preferred compositions include a compound that binds to thaumatin-like proteins and that reduces a concentration of glucose in an organism when the compound is administered to the organism at a concentration effective to reduce the concentration of glucose.

In alternative aspects of the inventive subject matter, it is contemplated that appropriate compositions and compounds need not be limited to a preparation from Hordeum vulgare, but may also include preparations from various plants other than Hordeum vulgare, and particularly contemplated alternative plants include Hordeum spec., and members of the poaceae family. While the preparation of contemplated compositions and/or compounds is preferably from plant extracts, it should further be appreciated that contemplated compositions and/or compounds may also be isolated from microorganisms (i.e., bacteria, fungi, yeasts, unicellular eucaryotic organisms) or animals, so long as contemplated compounds bind to a thaumatin-like protein and reduce a glucose concentration in an organism.

In contemplated embodiments of the inventive subject matter, contemplated compositions are identical with, or a derivative of, a molecule isolated from Hordeum vulgare. Derivatives can be advantageously developed to address issues of bioavailability, targeting and other specificity, efficacy, and reduction in toxicity. It is further contemplated that the molecule may be isolated from Hordeum vulgare through any procedure including malting, mashing, salt extraction, a buffer extraction, ethanol extraction, anion exchange chromatography, and molecular sieving. Still further, it is contemplated that the molecule is isolated from any part of the Hordeum vulgare or a plant seed of Hordeum vulgare. It is preferred that the molecule is isolated from a malted seed of Hordeum vulgare.

In still further alternative aspects, it should be appreciated that contemplated compounds may be isolated, purified to homogeneity, and the structure be elucidated. Consequently, it should be appreciated that contemplated compounds and/or compositions may be entirely (de novo) or partially synthesized/modified in vitro. For example, where contemplated compounds are partially synthesized, a precursor of contemplated compounds may be isolated from a plant or microorganism, and then be subjected to one or more steps to arrive at contemplated compounds. Alternatively, contemplated compounds may be modified in one or more synthetic steps to impart a particularly desirable physicochemical property. For example, contemplated compounds may be esterified with a polar compound (e.g, polyethylene glycol) to increase water solubility. In another example, contemplated compounds may be coupled to a resin or other material to control the rate of release to the organism.

Preferred contemplated compounds have a relatively low molecular weight, typically no more than 2000 Da, however, it should be recognized that the molecular weight may vary considerably and will predominantly depend on the source from which the compound is isolated, synthetic modifications, dimerizations and multimerizations. Likewise, it is contemplated that suitable compounds need not be limited to compounds having a UV absorption maximum at about 260 nm (which is characteristic for contemplated compounds isolated using the procedure outlined below), and various spectral characteristics other than a $UV_{260}$ peak are also suitable. Similarly, while contemplated compounds isolated from Hordeum vulgare are soluble in a lipophilic solvent at a concentration of at least 10 mg per milliliter, higher or lower solubilities are also contemplated and will typically depend on the source from which contemplated compounds are isolated, and/or on further chemical modifications of contemplated compounds. The term "lipophilic solvent" as used herein includes all solvents that have a miscibility with $H_2O$ of less than 10 vol %.

While it is generally preferred that contemplated compounds are chemically substantially pure (i.e., concentration of contemplated compounds greater than 90 wt %, preferably greater than 95 wt %, most preferably greater than 99 wt %), it should also be appreciated that contemplated compounds may be coupled to one or more than one molecule, and particularly contemplated molecules include thaumatin-like proteins. Thus, contemplated compositions include complexes between contemplated compounds and thaumatin-like proteins, and especially include complexes between contemplated compounds and thaumatin-like proteins as they are isolated from the appropriate sources (infra).

With respect to the glucose concentration, it is generally contemplated that the glucose concentration is a blood glucose concentration. However, further contemplated glucose concentrations also include concentrations of glucose covalently or non-covalently bound to molecules found within the organism, and especially contemplated alternative glucose concentrations include concentrations of glycosylated proteins (e.g., glycosylated hemoglobin or collagen).

While it is generally contemplated that suitable thaumatin-like proteins are isolated from *Hordeum vulgare*, alternative thaumatin-like proteins are also contemplated and include thaumatin-like proteins isolated from microorganisms, plants, and animals, which may or may not be expressed in a recombinant system. There are various protocols for isolation of thaumatin-like proteins known in the art (see e.g. Barre et al, Purification and structural analysis of an abundant thaumatin-like protein from ripe banana fruit. Planta. 2000 November; 211(6):791-9; Oh, et al., Isolation of a cDNA encoding a 31-kDa, pathogenesis-related 5/thaumatin-like (PR5/TL) protein abundantly expressed in apple fruit. Biosci Biotechnol Biochem. 2000 February; 64(2):355-62; Tattersall, et al. Identification and characterization of a fruit-specific, thaumatin-like protein that accumulates at very high levels in conjunction with the onset of sugar accumulation and berry softening in grapes. Plant Physiol. 1997 July; 114(3):759-69), and all the known protocols are considered suitable for use in conjunction with the teachings presented herein.

It should be especially appreciated that contemplated compositions not only reduce elevated blood glucose concentration in human suffering from NIDDM, but may also reduce blood glucose concentrations in individuals having elevated blood glucose concentrations for reasons other than NIDDM, including obesity, dietary effects, etc. It is especially contemplated that individuals with or without NIDDM will have a blood glucose concentration of at least 90 mg/dl, more preferably of at least 120 mg/dl, and most preferably of at least 200 mg/dl.

Furthermore, contemplated compositions have also been shown to advantageously reduce elevated blood lipid concentrations (infra), wherein blood lipids particularly include triglycerides, fatty acids, HDL-cholesterol, and LDL-cholesterol, and it is further contemplated that the reduction of blood lipids may be concomitantly with the reduction of blood glucose levels, or independent of the reduction of the blood glucose level.

In further aspects of the inventive subject matter, it should be appreciated that contemplated compositions may further comprise active or inactive ingredients, including compositions known to decrease a blood lipid concentration, and/or compositions known to decrease blood sugar concentrations. For example, alternative compositions may include at least one of a tocol, vitamins, and/or mineral preparations, GTF, metformin, sulfonylurea, and the like. Inactive ingredients include fillers, coloring agents, stabilizers, and the like.

Thus, an exemplary method of treating a person (e.g., diagnosed with NIDDM) having an increased blood concentration of glucose of approximately 150 mg/dl, and an increased blood concentration of total cholesterol of above 280 mg/dl, or more has one step in which contemplated compositions are provided. In a further step, the composition is administered to the person in a dosage effective to decrease the concentration of glucose.

With respect to the blood glucose level it is contemplated that a treatment according to the inventive subject matter need not be limited to blood glucose levels of approximately 150 mg/dl, but may also be indicated at many blood concentrations of glucose above 70-110 mg/dl. Although not wishing to be bound to a particular theory or mechanism, it is contemplated that the reduction in the blood glucose level may be due to an enhanced glucose uptake into the cell. However, it should be noted that compositions according to the inventive subject matter are non-GTF compositions. The duration for contemplated treatments may vary significantly, and suitable durations may be within the range of a single dose, but also for a predetermined period, including one week, several weeks, several months, and even several years. Consequently, it should be appreciated that compositions according to the inventive subject matter may also be prophylactically administered to a human to prevent hyperglycemia, or some form of dyslipidemia.

In still further aspects of the invention, contemplated compositions increase glucose uptake into a cell. It is contemplated that the cell may be any cell including a myocyte, or part of a tissue. It is further contemplated that the cell may be insulin dependent or insulin independent. Contemplated tissues are preferred to be in vivo, and may include liver tissue, skeletal muscle tissue, pancreatic tissue, and adipose tissue. It is further preferred that the cell is a myocyte and is insulin independent.

Contemplated compositions may be present in a medium surrounding the cell, such as the serum or interstitial fluids. It is further contemplated that the composition may increase glucose uptake into a cell when the compound is present in a medium surrounding the cell at a concentration of between 2-10 micrograms per milliliter. Furthermore, it is contemplated that the cell or the medium surrounding the cell is depleted of at least one of a nutrient and oxygen. The term "depleted" refers to less than 10% of a normally fit cell or less than 15% of a particular nutrient (i.e. glucose). Moreover, it should be appreciated that an increase in glucose uptake is reduced when the medium surrounding the cell comprises L-N-mono-methyl-L-arginine at a concentration of 300 micromoles per liter.

It is further contemplated that the composition may be modified to increase or decrease an increase of glucose uptake into a cell. Furthermore, it is contemplated that the composition may be modified to increase or decrease solubility in a solvent, chemical stability, or in vivo specificity.

In further alternative aspects of the inventive subject matter, the composition may also be administered to an organism other than a human, and particularly preferred alternative organisms include livestock (e.g., cattle, pigs, horses, etc.) and pets (e.g., dogs, cats, rodents, birds, etc.). With respect to contemplated compositions, the same considerations as described above apply.

It is especially contemplated that treatment according to the inventive subject matter may also result in significant weight loss, particularly in persons with obesity, NIDDM, or other condition associated with increased body weight. It is generally contemplated that the treatment according to the inventive subject matter is not limited to reduction of blood glucose alone, but may concomitantly (or by itself) include reduction of a particular lipid or lipid group. For example, slightly elevated total cholesterol (e.g., 220 mg/dl) may be an indication for treatment with the contemplated compounds. Alternatively, it is contemplated that an imbalance between HDL and LDL (i.e. LDL>>HDL) may be normalized employing a treatment according to the inventive subject matter. Similarly, while the total cholesterol in the patient need not be elevated, treatment with the contemplated method may still be indicated due to an elevated triglyceride level.

With respect to the dosage, form, and route of administration it is contemplated that there are many alternative oral preparations besides 3 oral daily doses of 500 mg. For example, where relatively high dosages are required, dosages may increase from 500 mg-5 g per day, and more. High dosages may also be required where the potency of an extract is relatively low. Likewise, in cases where low dosages (e.g., maintenance therapy) are required, or the extract has a comparably high potency, daily dosages between 500 mg and 25 mg, or less, are appropriate. Therefore, it is generally contemplated that among other parameters the patient's particular condition and the potency of the preparation will at least partially determine the frequency of application. For example, where high dosages are to be administered to the patient, more than 3 daily dosages are contemplated, including 4-6 and more. Where low dosages, especially dosages lower than 500 mg/day are contemplated, single, bidaily, or less frequent administrations are appropriate.

Of course it should also be recognized that the form of administration may vary considerably. For example, oral administration need not be limited to a tablet, and alternative oral administrations may include powders, gel-caps, syrups, gels, etc. Where oral administration is not desirable, it is further contemplated that alternative routes are also appropriate, including injections, transdermal, pulmonary or intranasal delivery.

EXAMPLES

The following examples provide various experimental procedures to make and use contemplated compounds according to the inventive subject matter. Examples 1 and 2 describe basic and improved procedures of producing compositions according to the inventive subject matter, respectively. The biological activity of the compounds isolated according to procedures in Examples 1 and 2 is described in Example 3 and 4, and Example 5 provides experimental support for specific binding of contemplated compounds to thaumatin-like proteins. Example 6 provides experimental procedures to determine the molecular weight of molecules in GMM. Example 7 provides experimental data for chromatographic fractions of GMM retentate, and example 8 provides experimental support for an increase of glucose uptake in L6 muscle cells of GMM permeate. Examples 9-22 present additional preferred embodiments that are among the inventive subject matter.

Example 1

Barley grains were malted according to procedures well known in the art of beer brewing (see e.g., Principles of Brewing Science, Second Edition, by George J. Fix; Brewers Publications; ISBN: 0937381748, or The Brewers' Handbook by Ted Goldhammer; KVP Publishers; ISBN: 0967521203). In order to extract soluble substances from the malt and to convert additional insoluble solids into soluble material through controlled enzymatic conversion, a step of mashing was subsequently applied to the ground malt (suspended in water) according to a typical brewer's schedule. The temperature cycles were as follows: Incubation at 40° C. for 60 min, incubation at 50° C. for 60 min, incubation at 60° C. for 60 min, incubation at 72° C. for 60 min, and incubation at 75°-80° C. for 60 min. Soluble portions of samples were separated from husks and other insoluble material and freeze-dried.

The freeze-dried barley extract obtained after mashing at 40° C. served as base for fractionation into its components. A first fractionation was achieved by preparative liquid chromatography using a DEAE-Sephacel column (2.6×20 cm) equilibrated with 50 mM phosphate buffer, pH 7.8. 150 mg of the freeze-dried sample was dissolved in 10 ml of buffer and placed on the column. A linear NaCl-gradient (0-0.5 M) was run at a flow rate of 10 ml/h. Fractions (2 ml each) were collected, and elution was monitored at 280 nm. The DEAE chromatography resulted in four distinct protein peak fractions: I—basic, II—neutral, III—and IV—acidic. Respective peak fractions were collected, desalted and concentrated by membrane ultra-filtration using a membrane cut-off pore size of 1000 Dalton, and concentrated corresponding fractions were checked for their capacity to influence yeast fermentation rate. The basic fraction I produced significant inhibitory effect (i.e., a reduction of the yeast fermentation rate), while the remaining three concentrated fractions were almost inert. As it could later be identified (data not shown), the main proteinaceous component in fraction I represent thaumatin-like proteins. It has been noticed during the membrane ultra-filtration of the pooled protein fractions I-IV (i.e., fractions obtained by ion exchange chromatography), that the filtrate of some fractions contains LMW (low molecular weight) substances with a UV absorbance maximum of approximately 260 nm. These observations prompted us to employ molecular sieving chromatography to separate these LMW substances from proteins in these fractions.

For that purpose, the four separated fractions by DEAE-Sephacel column I-IV were pooled and freeze-dried. Molecular sieving chromatography was performed on Sephadex G-75-50 column (2.8×80 cm) with 50 mM phosphate buffer, pH 7.8, containing 0.5 M NaCl (flow rate—12 ml/h, fractions 2 ml, elution recorded at 260 nm). LMW compounds with an absorbance near 260 eluted at relatively high elution volume. Where the separated fractions were individually subjected to molecular sieving on a Sephadex G-75-50 column, LMW compounds eluted near to the end of the separation, typically between 60th-80th fractions. These fractions were designated GMM-1, GMM-2 and GMM-4, and consist of LMW components.

All of GMM-1, GMM-2 and GMM-4 enhanced yeast fermentation, bound strongly and reversibly to thaumatin-like protein (bind to thaumatin-like proteins at low salt condition and release from thaumatin-like proteins at high salt condition), and reduced elevated blood glucose concentration and elevated blood lipid concentration in human diagnosed with NIDDM.

Example 2

20 g of malted barley flour was suspended in 80 ml of water and stirred over night at ambient temperature. The suspension was supplemented with 120 ml of 0.8 M NaCl solution and salt extraction was continued for 24 hours with stirring. An aqueous extract was separated from the suspension by vacuum filtration over a cellulose filter pad. Alternatively, citrate or other buffers are also contemplated suitable for preparation of an aqueous extract.

The filtered extract was freeze-dried or vacuum-evaporated. So obtained dry malt extract (yield approx. 12-14 g) contained 5.6 g of NaCl originating from the extracting solvent and a complex mixture of water-soluble barley components. The filtered freeze-dried extract was purified by extraction with two 50 ml portions of warm ethanol under vigorous mixing for two hours. The ethanolic extracts were filtered, combined, and evaporated to an oily residue in vacuum. The oily residue was re-dissolved in 15 ml of water and freeze-dried, resulting in a hard glassy yellowish product in a total amount of approx. 3 g.

The glassy yellowish product enhanced yeast fermentation, bound strongly and reversibly to thaumatin-like protein (bind to thaumatin-like proteins at low salt condition and release from thaumatin-like proteins at high salt condition), and reduced elevated blood glucose concentration and elevated blood lipid concentration in human diagnosed with NIDDM.

Thus, it should be recognized that contemplated compositions comprise a plant seed extract (preferably from *Hordeum vulgare*), wherein the plant seed is malted (preferably at a temperature between about 30° C. and 65° C.) and the extract is prepared from the malted plant seed using a protocol that includes an aqueous extraction step (e.g., using an aqueous buffer such as a citrate buffer), and that the extract reduces a glucose concentration in an organism when the extract is administered to the organism at a concentration effective to reduce the concentration of glucose.

Example 3

The biological activity of LMW fractions from Example 1 (GMM-1, GMM-2 and GMM-4) and the glassy yellowish product from Example 2 was monitored by quantification of brewers' yeast fermentation rate under anaerobic conditions using a modified Warburg method (Mirsky, N. et al., J. Inorg. Biochem. 13(1):11-21 (1980), which is incorporated by reference herein.

Figure 6:
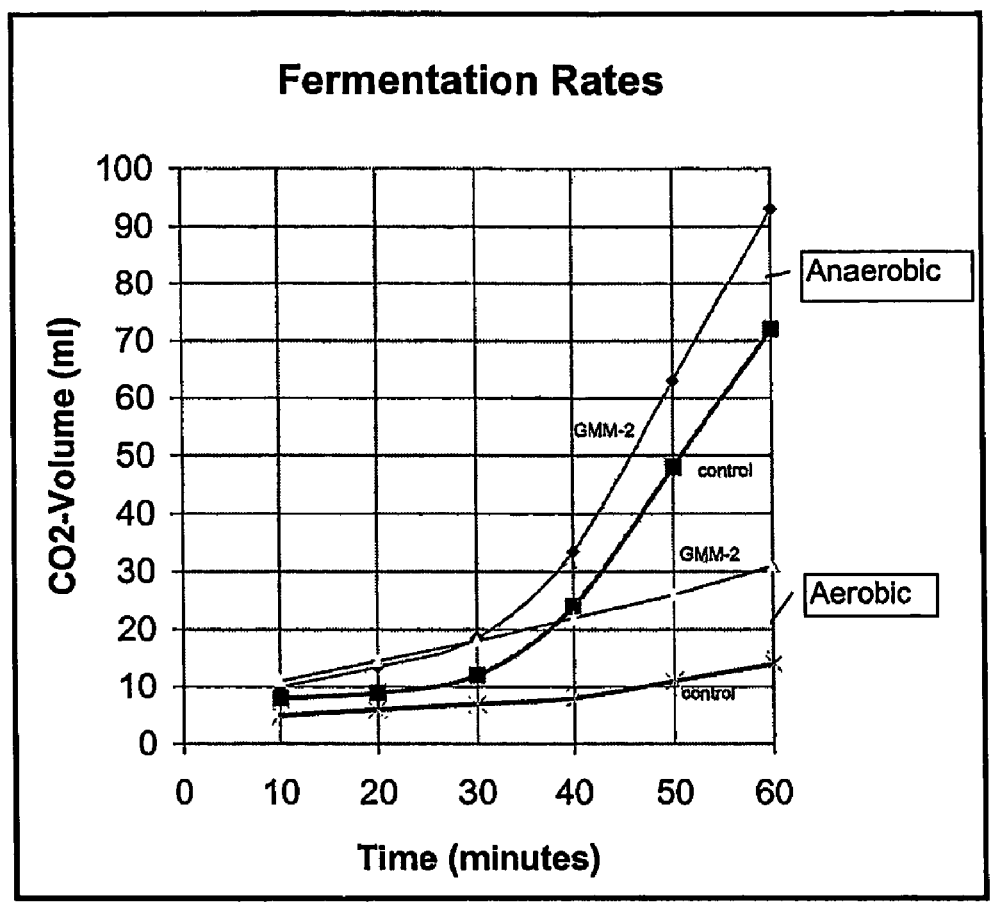
FIG. 6 is a graph depicting fermentation rates of yeast incubated with contemplated compounds at anaerobic and aerobic conditions.

Two grams of wet brewers yeast cells (about 20% dry weight) were suspended in fermentation medium (25 ml of 60 mM phosphate buffer, pH 5.7 and 10 ml of 5% (w/v) glucose solution), and aliquots of the products from example 1 or 2 were added to the fermentation medium for testing. Incubations were carried out in 50 ml fermentation flasks at 25° C. for 60 minutes. The fermentation rates were measured from the volume of generated $CO_2$. All of the tested LMW fractions or the product from Example 2 showed significant biological activity or bioactivity in that they increased the yeast fermentation rate in the range of about 20-40%. As used herein, a bioactive compound is one that increases or decreases fermentation. In a further experiment, the activity of GMM-2 was checked at aerobic conditions. Despite general restriction of yeast fermentation caused by combined effects of NaCl from buffer and air oxygen (Pasteur effect), the relative amount of generated $CO_2$ was doubled in comparison to the included control. The comparative results for GMM-2 fraction at anaerobic and aerobic conditions are shown below in FIG. 6. The results conclusively prove modulating activity of the isolated LMW substances on yeast metabolism. Furthermore, these results illuminate the additional utility of the contemplated compounds for use where enhanced rates of fermentation are desired, for example, but not limited to, the application of fermentation reactions in the production of commercially important products.

Example 4

The product obtained in Example 2 was examined for use in humans diagnosed with NIDDM. 25 men were recruited from an outpatient clinic (Endocrinology Department). Mean age within the group was 51 yr, ranging from 36 to 74. Medical records were screened to exclude diabetics taking insulin or oral hypoglycemic agents. All of the subjects agreed to maintain their usual eating habits and health-related behaviors throughout the study. The experimental treatments were run over a period of six month. The participants were instructed to take the preparation in 3 oral daily doses of 1,000 mg each in a tablet form.

All subjects were tested for plasma glucose, glycosylated hemoglobin HbAc1, triglycerides and cholesterol before supplementation and throughout the study at biweekly or monthly intervals depending on type of tests. The subjects were subdivided into groups according to patterns given below:

Plasma glucose: According to the plasma glucose levels the subjects were subdivided in three groups for differentiation of the effects: I—up to 8 mMol/L; II—8-10.5 mMol/L and III—above 10.5 mMol/L of plasma glucose concentration. Glycosylated hemoglobin (HbAc1): According to the HbAc1 levels the subjects were divided in two groups: I—below 10% and II—above 10% of the modified hemoglobin. The test results related to glycemia, before and after treatment, are shown in FIG. 4A.

A further set of clinical studies was performed with 10 human volunteers following a similar protocol as outlined above. In this second experiment, blood glucose was measured fasting and postprandial over a period of 90 days, and the results are shown in FIG. 4B. As can be clearly seen, administration of contemplated compounds results in a decrease of fasting and/or postprandial blood glucose of at least 5%, more typically of at least 10%, and most typically of at least 20%. Similarly, the levels of glycosylated hemoglobin was reduced after administration of contemplated compounds at least 5%, more typically at least 20%, and most typically at least 50%.

The lipid status of the subjects diagnosed with NIDDM was determined before and after treatment by testing plasma level of triglycerides, and cholesterol (as total, LDL and HDL form). The test results shown in FIGS. 5A and 5B include subjects with disturbed lipid metabolism due to diabetic disease.

The lipid status of the subjects as shown in FIG. 5A includes plasma levels of triglycerides, the ratio of triglycerides over total cholesterol, and the ratio of LDL/HDL. The latter two ratios are known as atherosclerotic risk factors. As can be seen from FIG. 5A, administration of contemplated compounds resulted in a reduction of triglycerides of up to 50%, and a significant reduction of about 1-20% of the ratio of triglycerides to HDL cholesterol, with an even more dramatic reduction of the ratio between LDL to HDL cholesterol (about 40%). The lipid status as shown in FIG. 5B includes further results of ten test patients after administration of contemplated compounds and/or compositions over a period of 90 days.

Example 5

Figure 3:
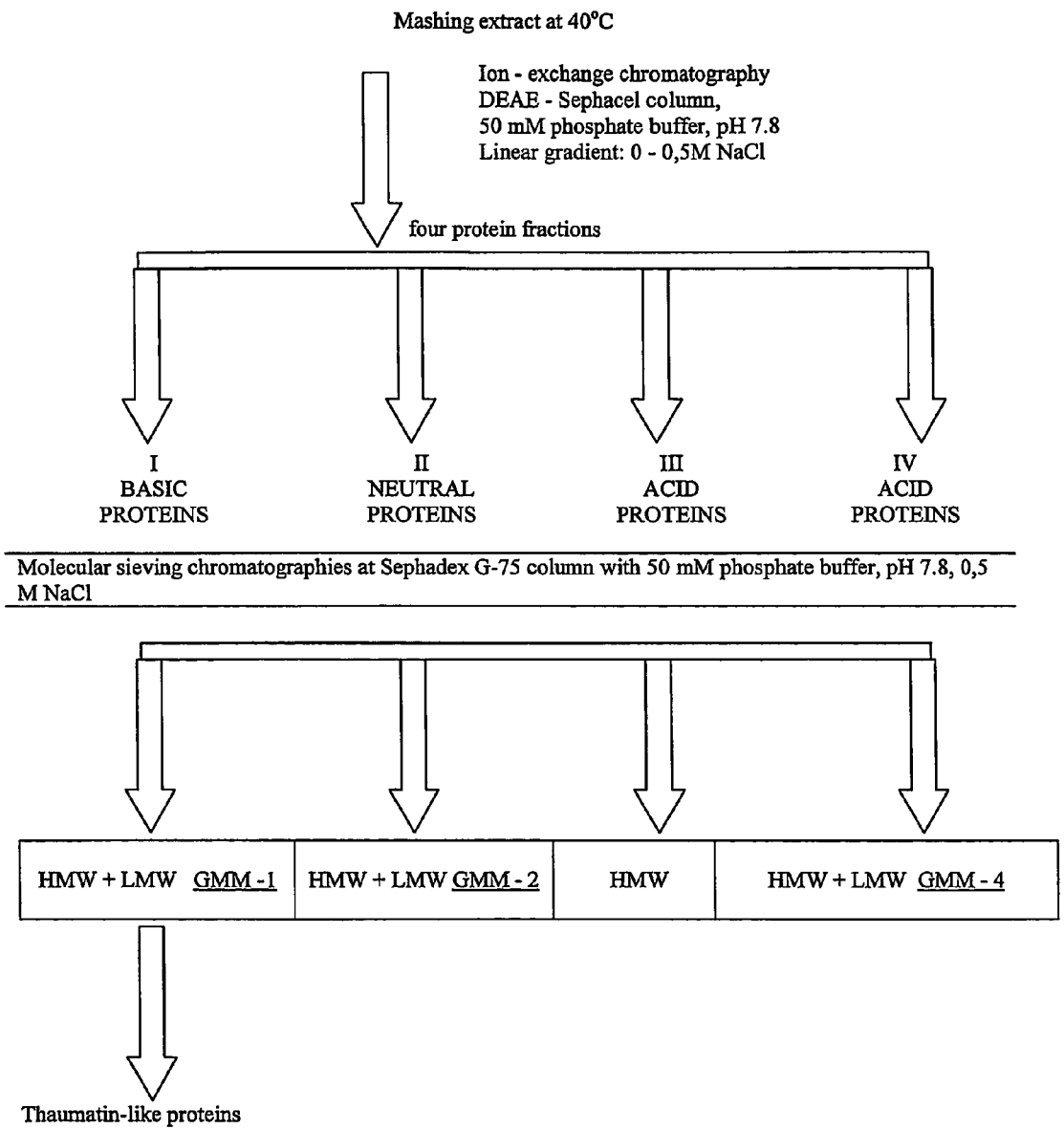
FIG. 3 is a schematic showing an exemplary preparation of contemplated compounds and thaumatin-like proteins.

Thaumatin-like proteins were prepared following the procedure as generally outlined in Example 1 and FIG. 3. So isolated thaumatin-like proteins were subjected to repeated molecular sieving in a membrane concentrator using a membrane with a molecular weight cut off of about 1000 Dalton. After a first round of filtration of the protein preparation, 99 ml of buffer (50 mM phosphate buffer, pH 7.8, 0.5 M NaCl) were added to about 1 ml of retentate (i.e. the thaumatin-like protein fraction), and three subsequent rounds of filtration were performed with the same buffer to remove remaining GMM-compounds (i.e., herein presented compounds that reduce elevated glucose) from the thaumatin-like protein preparation. UV absorbance of the filtrate was monitored at 260 nm and the biological activity of sample volumes from the filtrate was tested according to protocols outlined in Example 3. Such prepared thaumatin-like proteins were desalted by membrane filtration employing NaCl-free buffer (50 mM phosphate buffer, pH 7.8), and further used in the following procedure:

To 1 ml of a desalted thaumatin-like protein solution (10 mg/ml), 1.0 ml of a GMM-1 solution (1 mg/ml) was added, and the mixture was incubated at room temperature for 2 hrs. After 2 hrs, 98 ml of 50 mM phosphate buffer, pH 7.8 were added to the mixture and unbound GMM-1 was removed by 3 subsequent rounds of ultrafiltration (each round 1:100 by volume) with buffer.

The thaumatin-like protein with the bound GMM-1 was labeled Sample 1. Sample 1 was then subjected to a molecular sieving chromatography using a Sephadex G-75 column with 50 mM phosphate buffer, pH 7.8, 0.5 M NaCl as solvent, in which a low molecular weight fraction eluted with an absorbance of 260 nm separate from a higher molecular weight fraction of the thaumatin-like protein with absorbance of 280 nm. The low molecular weight fraction was concentrated, desalted, and brought to a volume of 1.0 ml and labeled Sample 2. Samples 1 and 2 were then tested for biological activity employing a procedure as outlined in Example 3. While Sample 1 did not increase the rate of fermentation, Sample 2 significantly increased the rate of fermentation in both aerobic and anaerobic experimental conditions, thereby clearly demonstrating the reversible binding of GMM-1 to a thaumatin-like protein. The same procedure was repeated with GMM-2 and GMM-4. The obtained results were similar to the presented GMM-1 experiment.

Thus, specific embodiments and applications of compositions and methods to reduce glucose concentrations in an organism have been disclosed. It should be apparent, however, to those skilled in the art that many more modifications besides those already described are possible without departing from the inventive concepts herein. The inventive subject matter, therefore, is not to be restricted except in the spirit of the appended contemplated claims. Moreover, in interpreting both the specification and the contemplated claims, all terms should be interpreted in the broadest possible manner consistent with the context. In particular, the terms "comprises", and "comprising", should be interpreted as referring to elements, components, or steps in a non-exclusive manner, indicating that the referenced elements, components, or steps may be present, or utilized, or combined with other elements, components, or steps that are not expressly referenced.

Example 6

GMM was dialyzed in order to determine the molecular weight distribution of active GMM components and to purify and concentrate the active components. A series of experiments was performed in portions of 3 g of GMM preparation per one tube. GMM samples were dissolved in 40 ml of water and dialyzed against 500 ml of water for 24 hours. External water was replaced with fresh water after 24 hours, for better separation. The external water portions were combined, concentrated in a vacuum, centrifuged, and evaporated to dryness, resulting in permeate. The contents of the dialysis tubes were centrifuged and evaporated to dryness in a vacuum, resulting in retentate.

The percentage ratio of permeate to retentate was 58.5:25.1, with 16.4 corresponding to insoluble materials from both retentate and permeate. This insoluble part was discarded.

Figures 7, 8:
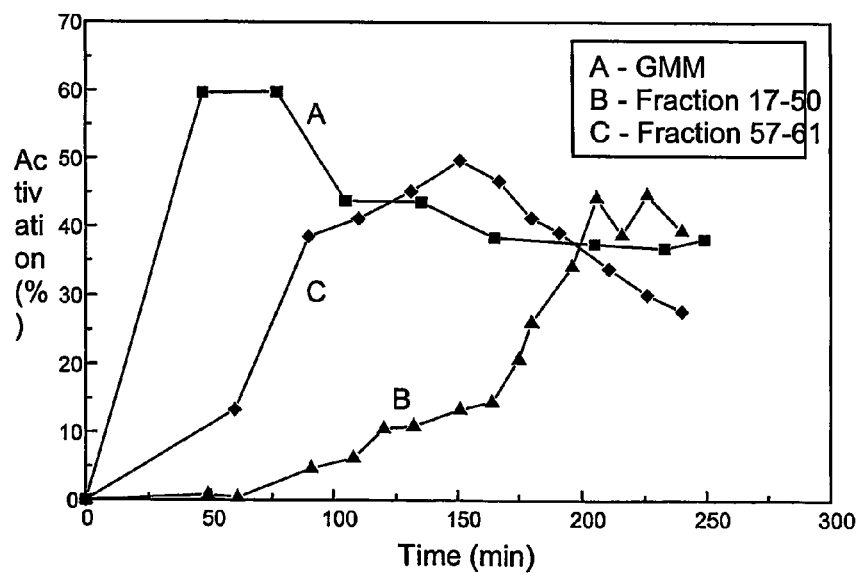
FIG. 7 is a table depicting intermediate activities by hours of retentate (high molecular weight) and permeate (low molecular weight) of GMM sample after dialysis.
FIG. 8 is a graph depicting fractions of eluates from the retentate portion of GMM sample.

The kinetics (rate of action) of the two soluble fractions in yeast fermentation is shown in FIG. 7. FIG. 7 shows that at least two types of active compounds in GMM are present. These two types include: high molecular weight (HMW, retentate) substance(s) with an increase of activity with the progress of the fermentation process, and low molecular weight (LMW, permeate) substance(s) with an early activity decreasing with progress of fermentation. In addition, the permeate kinetic is overlapped with retentate activity. This may have been due to the nononselective pore size of the dialysis tubing may have allowed for partial passage of retentate components through the pores. This phenomenon has been repeated in repetitive dialysis cycles. The results indicate that the molecular weight of the permeate compounds is close to 2,000 Daltons.

Moreover, the retentate activity results in a significant increase of yeast biomass in a range of 44% over the control. The results may indicate that the retentate GMM fraction acts at a gene level leading to cell multiplication, while the permeate GMM fraction most probably exerts its action through an enhanced glucose uptake in a non-insulin dependent pathway.

Example 7

The retentate sample from Example 6 was subject to gel permeation chromatography with Sephadex G-75-50 at column of 2×80 cm using 50 mM phosphate buffer, pH 7.8. The GMM/R samples were 40-50 mg dissolved in the buffer. The eluates were fractionated in the fraction collector in 15 minutes intervals, giving 1.5 ml fractions. The elution was traced by spectrophotometric measurement at and absorbed at 280 nm.

Yeast activity tests were then run using Barometric methods, which were more convenient than Gravimetric methods. The tests were run parallel and simultaneous to the control. The eluted fractions were then pooled in three successive sections: Section 1—fractions 17-50; section 2—fractions 51-60; and section 3—fractions 61-70.

An aliquot of fraction 17-50 was used to test for yeast activity, shown in FIG. 8. The active components in FIG. 8 were characterized with late activity development. The early position of the elution pattern in FIG. 8 shows indicates that the size of the components in fraction 17-50 was above 12,000 d. The remaining aliquots of fraction 17-50 was dialyzed against water in dialysis tubing with a 12,000 d cut-off. The retained content in the tube was analyzed for yeast activity and showed relatively strong inhibition, indicating the presence of active components with a molecular weight ranging between 2000 and 12,000 d.

An aliquot of fraction 51-60 was also tested for yeast activity and resulted in early activity development. Additionally, an aliquot of fraction 61-70 was tested for yeast activity and resulted in the strongest inhibitory effect among the three fractions. These data are not shown in the figures.

The eluted fractions were then pooled in five successive sections:

| | |
|---|---|
| Section 1 | fractions 18-32 |
| Section 2 | fractions 33-46 |
| Section 3 | fractions 47-56 |
| Section 4 | fractions 57-61 |
| Section 5 | fractions 61-80 |

Figure 10:
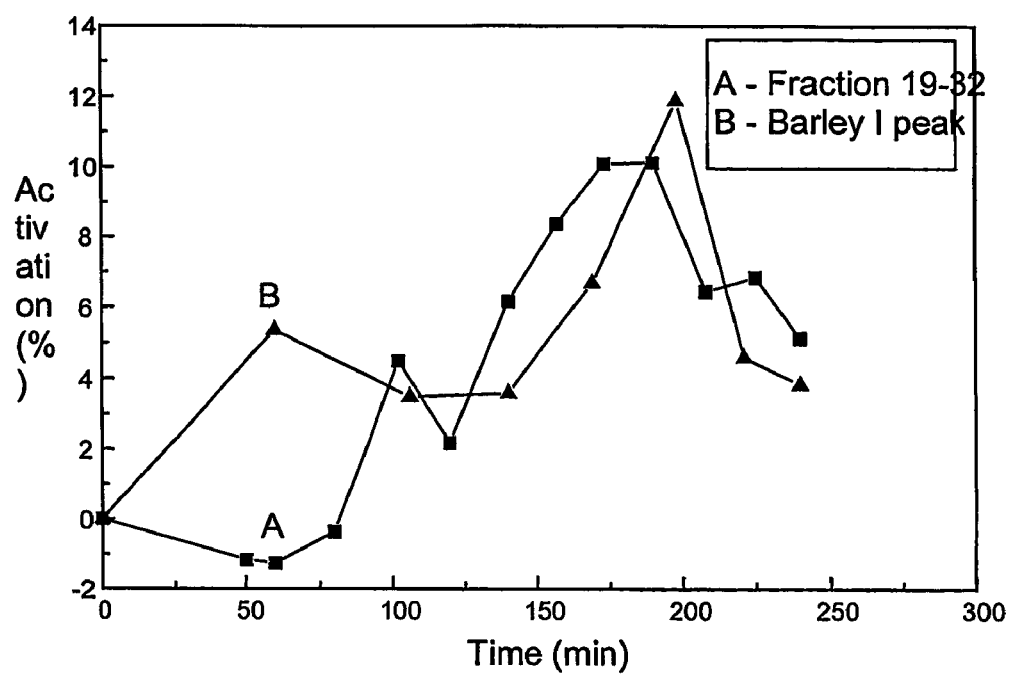
FIG. 10 is another graph depicting fractions of eluates from the retentate portion of GMM sample.

The sections were further analyzed for yeast activity. Fractions 19-32 showed a late activity development, as seen in FIG. 10. That result indicates that fraction 19-32 may have a high molecular weight above 20,000 d. A matching protein in the brewer's barley extract elutes at the same position on GP chromatography. That protein is not abundant in the extract, and has a molecular weight above 12,000 d because it does not release its activity on dialysis with 12,000 d cut-off tubings. The yeast activity profiles of two leading proteins are shown comparatively in FIG. 10.

Fractions 33-46 and fractions 47-56 were tested for yeast activity and showed an inhibitory effect.

Figure 9:
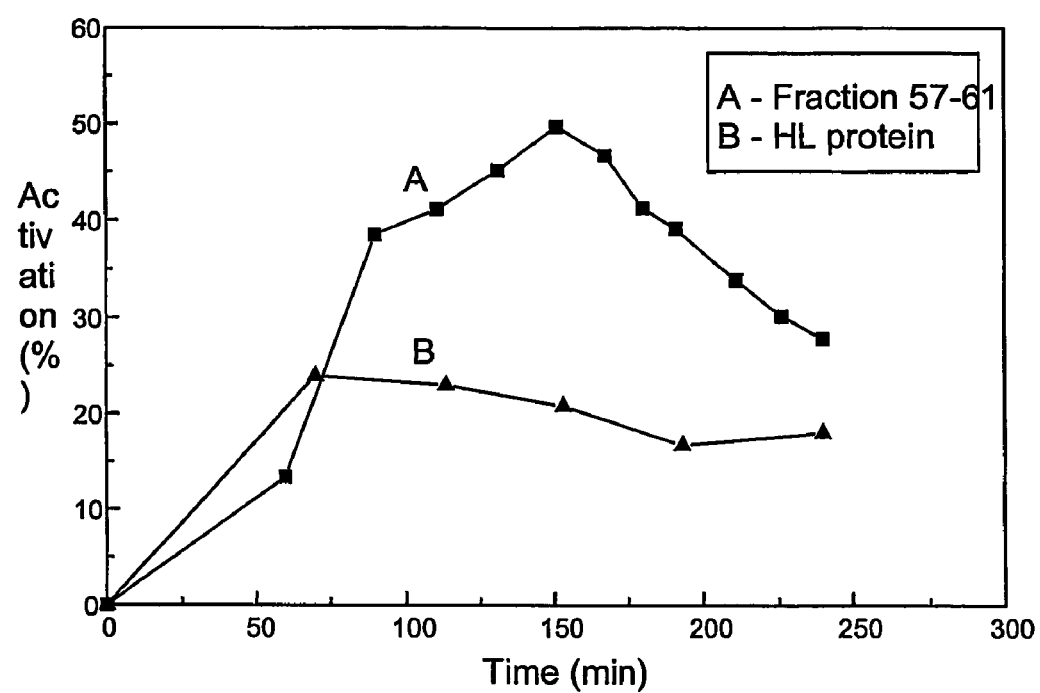
FIG. 9 is another graph depicting fractions of eluates from the retentate portion of GMM sample.

Fractions 57-61 were tested for yeast activity and showed early activity development, as seen in FIGS. 8 and 9. The position of this protein coincides with the position of brewer's barley HL-protein known to carry UV absorbing ligands at 265 nm. Past tests have shown that the HL-protein releases its ligands in the presence of salt in a 0.5M concentration. The HL-protein has a molecular weight of 14,000 d. FIG. 9 shows comparative yeast fermentation activities of HL-protein and its matching component of GMM at Fractions 57-61. The amount of HL-protein in the test was as low as 5 mg.

Thus, chromatographic fractionation of GMM retentate by gel permeation size exclusion revealed the presence of macromolecular species in the GMM preparation, most of which were proteins. Some of the proteins in the GMM retentate showed a significant inhibiting action on the yeast fermentation. Two macromolecular components were detected with apparent yeast fermentation activity. A peak in activity was located in the first portion of an elution pattern, which belonged to a molecular species passing through dialyzing membranes with a 12,000 d cut-off.

Example 8

The permeate portion of GMM was tested for glucose uptake in L6 muscle cells. L6 cells were grown as monolayers in Dulbecco's modified Eagle's medium (DMEM) containing 1 mM glutamine, 1 mM pyruvate and 25 mM glucose. The medium was supplemented with 5% fetal calf serum (FCS). Experiments were undertaken in 48-well plates seeded from pre-confluent flasks with 50 000 cells per well. The cells were grown to confluence and the medium was changed to DMEM containing 0.5% FCS and 2.5 mM glucose (L6 Myo Medium) for at least 76 hrs to induce differentiation of L6 cells and formation of L6 myotubes. Myotubes were then incubated with test substances for 30 minutes—Protocol SMM, or in Dulbecco's PBS supplemented with 20 mM Hepes and 2 mM glucose without serum—Serum-free Medium (SFM) Protocol as described by Fryer et al. (Activation of glucose transport by AMP-activated protein kinase via stimulation of Nitric oxide synthase, Diabetes, 49(12), 1978-85, 2000, Fryer LGD, et al, herein incorporated by reference in its entirety.).

Next, 30 uM of 2-NBDG was added for 2 minutes at 22 C. Subsequently, cell culture medium was removed and cells were washed twice with cold DPBS. Then, cells were lysed in 0.5% SDS. Fluorescence was measured at 466/542 nm (excitation/emission) using 100 ul of cell lysate in 2 ml of water.

Figure 11:
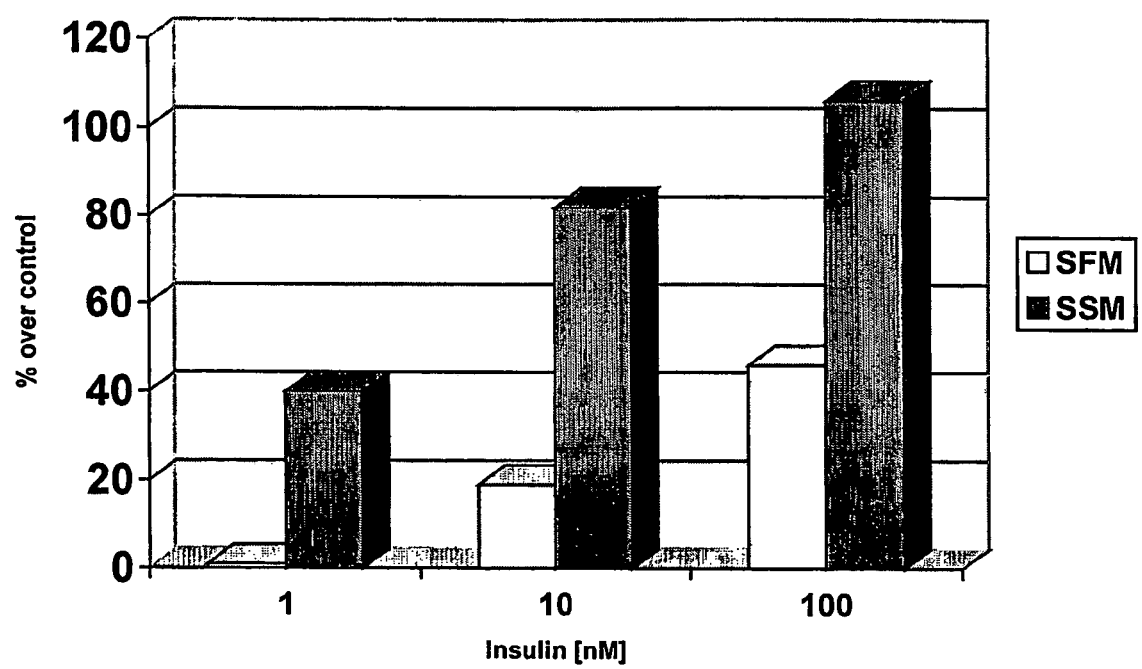
FIG. 11 is a graph depicting L6 cells treated with insulin in serum-free and serum-supplemented medium.

In FIG. 11, L6 cells treated with insulin in serum-free medium (DPBS) responded up to 40-50% glucose uptake increase. However, treatment of L6 with insulin in culture medium supplemented with 0.5% FCS(SSM) increased glucose uptake up to 100-120% by average. These results may suggest that muscle cells are more sensitive to insulin in presence of serum.

Figure 12:
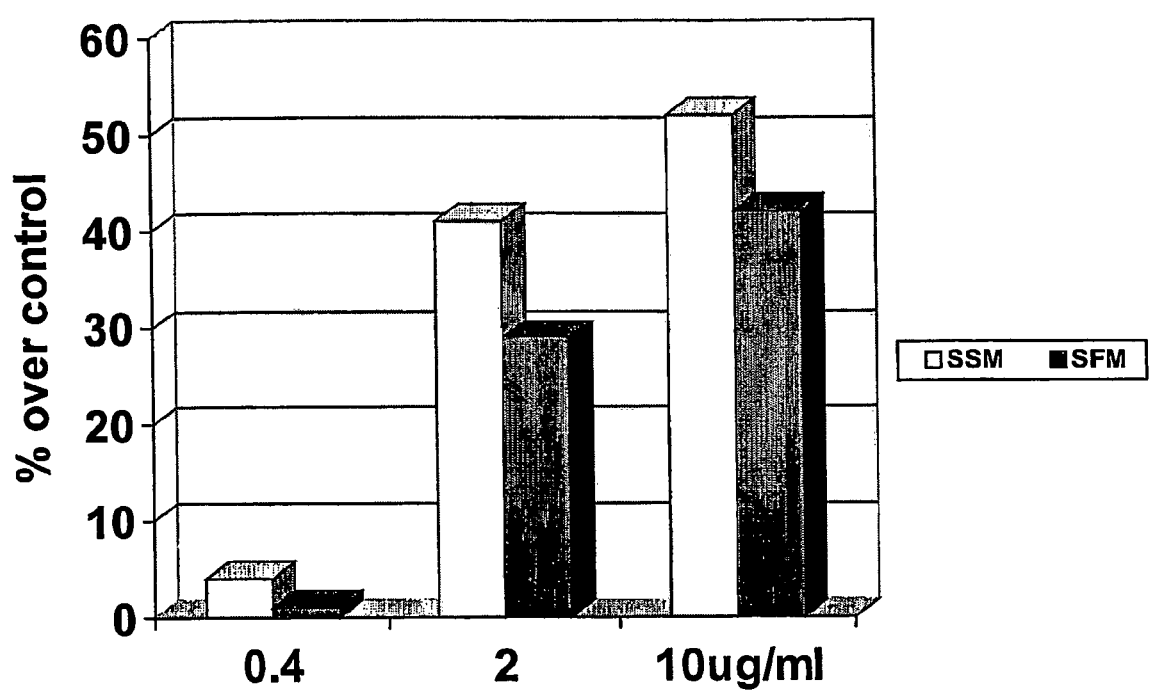
FIG. 12 is a graph depicting the effect of the permeate portion of GMM sample on glucose uptake in L6 cells.

FIG. 12 shows the effect of permeate on glucose uptake in L6 cells. Cells were cultured, and treated in L6 Myo Medium (SSM)—SSM Protocol or in serum-free medium (SFM—DPBS containing 20 mM Hepes, 2 mM glucose)—SFM Protocl as described by Fryer et al. Glucose uptake was measured by adding 30 uM of 2-NBDG for 2' at 22 C. Experiments were performed in duplicates.

Figure 13:
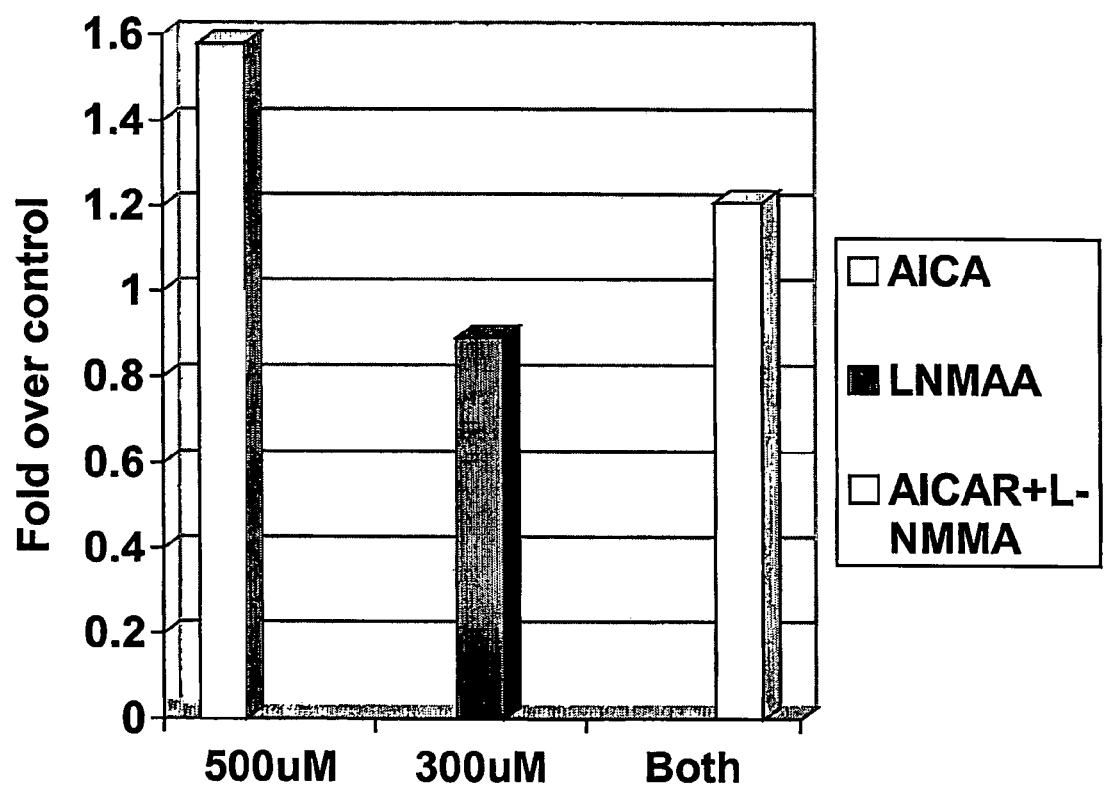
FIG. 13 is a graph depicting the effect of AICA, L-NMMA, and AICAR+L-NMMA on glucose uptake.

FIG. 13 shows the effect of AICA on the stimulation of glucose uptake and the effect of L-NMMA on the inhibition of glucose uptake. Similar effects are described by Fryer et al (Activation of glucose transport by AMP-activated protein kinase via stimulation of Nitric oxide synthase, Diabetes, 49(12), 1978-85, 2000, Fryer LGD, et al, herein incorporated by reference in its entirety). The permeate cells were pre-treated with L-NMMA for 30'in DPBS and subsequently treated with AICA for 30 minutes. Glucose uptake was measured after the treatment in 22 C for 2'.

In general, glucose transport in skeletal muscle is stimulated by two distinct stimuli, which are insulin and exercise. Recently it has been shown that AMP-activated protein kinase (AMPK) is activated by exercise in skeletal muscle. Pharmacological activation of AMPK by AICAR (5-amino-4-imidazolecarboxamide riboside) leads to an increase in glucose uptake. Interestingly, treatment of skeletal muscle cells with Nitric Oxide Synthase (NOS) inhibitors such as L-N-mono-methyl-L-arginine (l-NMMA) or L-N-nitro-L-arginine methyl ester (L-NAME) completely blocks the increase the glucose transport after activation of AMPK.

Figure 14:
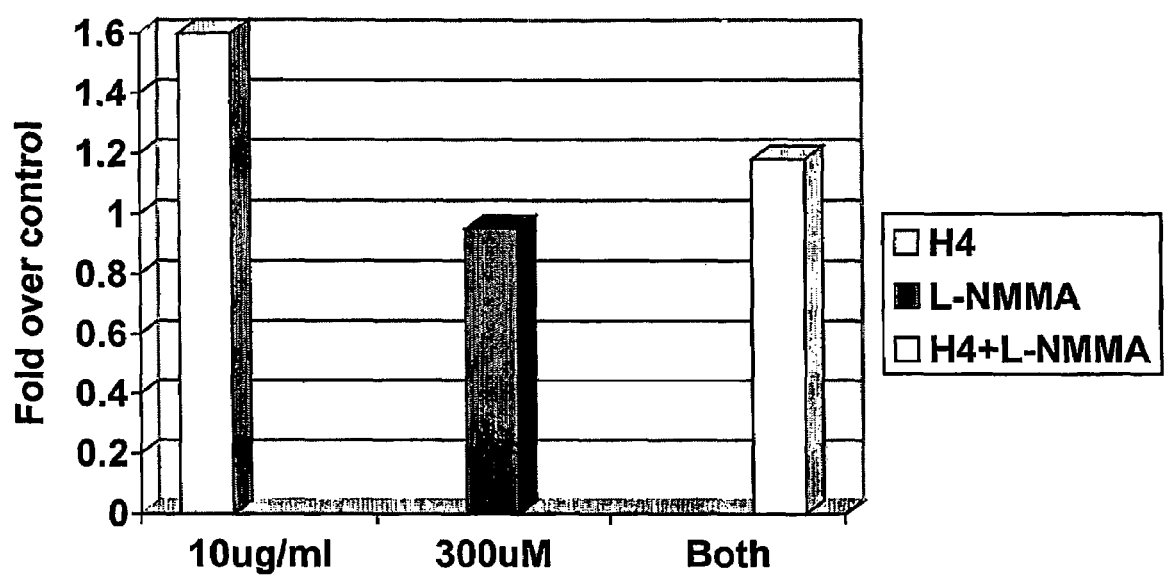
FIG. 14 is a graph depicting the effect of the permeate portion of GMM sample and the effect of the permeate portion+L-NMMA on glucose uptake.

In the study represented by FIG. 14, AICA was used because AICAR is not commercially available. AICA is a precursor of AICAR and it is metabolized in muscle cells to AICAR resulting in increase glucose uptake.

L-NMMA has been used in the experiment to verify whether GMM-induced glucose transport in L6 cells is or is not inhibited by NOS inhibitors, thus mimicking AICAR-induced mechanism of increased glucose transport. Fryer's experimental set up was adopted, consisting of pre-treatment of cells with inhibitor for 30 minutes in DPBS and after that with agonists like AICAR or in our case GMM for next 30 minutes at 37 C before performing glucose uptake.

In FIG. 14, permeate cells were tested to determine whether permeate-induced glucose uptake could be inhibited by L-NMMA at the same concentration as that used for inhibition of the AICA effect on glucose uptake. FIG. 14 shows that L-NMMA inhibits the effect of permeate on increased glucose uptake in L6 muscle cells in vitro. The L6 cells were pre-treated with L-NMMA in DPBS for 30 minutes and subsequently treated with GMM alone or GMM was added to cells treated with the inhibitor for next 30 minutes. Glucose uptake was measured at 22 C for 2 minutes.

According to the results in FIG. 14, pretreatment of L6 cells with L-NMMA at a concentration of 300 uM blocks GMM-induced of glucose transport under these experimental conditions. It may suggest that GMM works through the AMPK pathway in a similar fashion to AICAR. Such a mechanism of action has also been recently suggested for metformin, which is a drug approved for and widely prescribed in the treatment of patients suffering from non-insulin dependent diabetes mellitus (NIDDM), a disease characterized in part by diminished glucose uptake (Journal of Clinical Investigation, Vol. 108, No. 8, pages 1167-1174, herein incorporated by reference in its entirety.)

Example 9

Conditions and disorders associated with AMPK regulation of liver are among those treatable by administering a composition comprising a compound that activates AMPK. Acetyl-CoA carboxylase (ACC) and 3-hydroxy-3-methyl-glutaryl-CoA reductase (HMGR) are two classical targets for the AMPK system, catalyzing the key regulatory steps in fatty acid and sterol synthesis, respectively (Winder et al, Am J Physiol, 2777: E1-10, 1999, herein incorporated by reference in its entirety.) Activation of AMPK serves to inhibit both these lipid biosynthetic pathways, as well as triglyceride synthesis. Moreover, it is suggested that activated AMPK inhibits the L-type pyruvate kinase and fatty acid synthase gene expression. Inactivation of ACC in the liver cell also leads to decreases in the concentration of the product of ACC, i.e., malonyl-CoA, which has marked effects on fatty acid oxidation. Malonyl-CoA is a potent inhibitor of carnitine palmitoyltransferase-1 (CPT-1), the "gatekeeper" for entry of fatty acids into the mitochondria. In the liver, fatty acid oxidation can be considered to be an essential component of the pathway for synthesis of ketone bodies: increases in fatty acid oxidation lead to increased hepatic ketogenesis. Administering the composition to activate AMPK in the liver would result in decreases in fatty acid, triglyceride, and sterol synthesis and increases in fatty acid oxidation and ketogenesis. Thus, treatment with the composition to increase AMPK activity is useful in reducing fatty acid synthesis, sterol synthesis, triglyceride synthesis and fatty acid synthase gene expression, and in ameliorating disorders that are characterized by elevations in one or more of these pathways or mechanisms, or that are exacerbated by the effects of one or more of these pathways or mechanisms, as would be recognized by one of skill in the art. Treatment with the composition to increase AMPK activity is also useful in increasing fatty acid oxidation and ketogenesis where increased ketogenesis is desired as would be recognized by one of skill in the art.

Example 10

Conditions and disorders associated with AMPK regulation of fat cell metabolism are among those treatable by administering a composition comprising a compound that activates AMPK Hormone-sensitive lipase (HSL) is a target for AMPK in adipose tissue. (Ibid.) Activation of AMPK has been shown to inhibit lipogenesis by phosphorylation of ACC and also to inhibit isoprenaline-stimulated lipolysis. Thus, treatment with the composition to increase AMPK activity is useful in inhibiting lipogenesis and isoprenaline-stimulated lipolysis, and in ameliorating disorders that are characterized by elevations in one or both of these pathways, or that are exacerbated by the elevations in one or both of these pathways, as would be recognized by one of skill in the art.

Example 11

Conditions and disorders associated with AMPK regulation of insulin secretion are among those treatable by administering a composition comprising a compound that activates AMPK. Activated AMPK is thought to inhibit insulin secretion. (Ibid.) Since the contemplated compounds activate AMPK, treatment with the composition is useful in decreasing insulin secretion and in ameliorating disorders that are characterized by elevated insulin secretion, or that are exacerbated by insulin secretion, as would be recognized by one of skill in the art.

Example 12

Conditions and disorders associated with AMPK regulation of muscle metabolism and glucose uptake are among those treatable by administering a composition comprising a compound that activates AMPK. The effect of contraction on glucose uptake in muscle is well documented. It has been observed that either of exercise or electrical stimulation of muscle increases AMPK activity and also increases glucose uptake. It has also been observed that glucose uptake is increased by chemical activation of AMPK with AICA-riboside. Based on these observations, it has been hypothesized that muscle contraction plays a role in stimulating glucose uptake in muscle, where one mechanism underlying increased uptake stems from activated AMPK increasing GLUT-4 translocation from microvesicles to sarcolemmal membranes in muscle. (Ibid.) Thus, treatment with the composition to increase AMPK activity is useful in enhancing glucose uptake in muscle cells, and in ameliorating disorders that are characterized by decreased glucose uptake in muscle cells, or that are exacerbated by the effects of decreased glucose uptake in muscle cells, as would be recognized by one of skill in the art.

Example 13

Conditions and disorders associated with AMPK regulation of cytoplasmic concentrations of HuR are among those treatable by administering a composition comprising a compound that activates AMPK. HuR is an RNA binding protein that functions to stabilize a variety of target mRNA transcripts, including those encoding p21, cyclinA and cyclinB1. It has been shown that the presence of activated AMPK results in reduced levels of cytoplasmic HuR, and in turn, in reduced concentrations and half-lives of mRNA encoding p21, cyclinA and cyclinB1. (Mol Cell Biol, 22(10):345-36, 20002, herein incorporated by reference in its entirety) Thus, treatment with the composition to increase AMPK activity is useful in reducing levels of cytoplasmic HuR, and in turn, in reducing concentrations and half-lives of a variety of target mRNA transcripts, including but not limited to those encoding p21, cyclinA and cyclinB1, and in ameliorating disorders that are characterized decreased levels of HuR and its target transcripts, or that are exacerbated by the effects of decreased levels of HuR and its target transcripts, as would be recognized by one of skill in the art.

Example 14

Conditions and disorders associated with AMPK regulation of glucocorticoid-induced apoptosis are among those treatable by administering a composition comprising a compound that activates AMPK. Activated AMPK has been shown to provide protection against glucocorticoid-induced apoptosis and to restore cell viability and inhibit DNA laddering in dexamethasone-treated thymocytes. (Biochem Biophys Res Commun, 243(3):821-6, 1998, herein incorporated by reference in its entirety) Furthermore, activated AMPK has been shown to provide protection against dexamethasone-induced activation of caspase 3-like enzymes, which are believed to play a pivotal role in apoptotic cell death. Thus, treatment with the composition to increase AMPK activity is useful in providing protection against glucocorticoid-induced apoptosis as would be recognized by one of skill in the art, and in ameliorating disorders that are characterized by increased glucocorticoid-induced apoptosis, or that are exacerbated by glucocorticoid-induced apoptosis, as would be recognized by one of skill in the art.

Example 15

Conditions and disorders associated with AMPK regulation of cellular responses to stresses, including ischemia, are among those treatable by administering a composition comprising a compound that activates AMPK. In several nonvascular tissues in which it has been studied, AMPK appears to modulate the cellular response to stresses such as ischemia. In liver and muscle, AMPK phosphorylates and inhibits acetyl CoA carboxylase (ACC), leading to an increase in fatty acid oxidation; and in muscle, its activation is associated with an increase in glucose transport. Furthermore, incubation of human umbilical vein endothelial cells (HUVEC) with an AMPK activator has been shown to cause a 5-fold activation of AMPK, which was accompanied by a 70% decrease in ACC activity and a 2-fold increase in fatty acid oxidation. (Biochem Biophys Res Commun, 265(1): 112-5, 1999, herein incorporated by reference in its entirety) However, in this same study, glucose uptake and glycolysis, the dominant energy-producing pathway in HUVEC, were diminished by 40-60% under these conditions. Despite this, cellular ATP levels were increased by 35%. Thus, treatment with the composition to increase AMPK activity is expected to result in major alterations in endothelial cell energy balance, which are useful in providing protection against cellular stresses in conditions including ischemia, as would be recognized by one of skill in the art.

Example 16

Conditions and disorders associated with adipogenesis are among those treatable by administering a composition comprising a compound that activates AMPK. The AMPK activator, 5-aminoimidazole-4-carboxamide ribonucleoside (AICAR), has been found to inhibit the differentiation of 3T3-L1 adipocytes, if added at an early phase of differentiation. (Biochem Biophys Res Commun, 286(5):852-6, herein incorporated by reference in its entirety). AICAR blocks the expression of the late adipogenic markers, fatty acid synthase and acetyl-CoA carboxylase, and of the transcription factors, C/EBPalpha and PPARgamma. It also inhibits early clonal expansion of pre-adipocytes, prevents the fall in C/EBPbeta expression during the intermediate stage of differentiation and inhibits the late phase expression of CHOP-10, an antagonist of C/EBPbeta. Thus, given the inhibitory role for AMPK in the process of adipose differentiation, treatment with the composition to increase AMPK activity is useful in inhibiting adipogenesis as would be recognized by one of skill in the art, and in ameliorating conditions and disorders that are characterized by increased adipogenesis, or that are exacerbated by adipogenesis, as would be recognized by one of skill in the art.

Example 17

Conditions and disorders associated with metabolic and excitotoxic insults relevant to the pathogenesis of several different neurodegenerative conditions are among those treatable by administering a composition comprising a compound that activates AMPK. It is well known that the brain has a high metabolic rate and is sensitive to changes in the supply of glucose and oxygen. The expression of AMPK in embryonic and adult brain and its role in modifying neuronal survival under conditions of cellular stress have been investigated. (J Mol Neurosci, 17(1): 45-58, 2001, herein incorporated by reference in its entirety) Catalytic (alpha1 and alpha2) and noncatalytic (beta2 and gamma1) subunits of AMPK are present at high levels in embryonic hippocampal neurons in vivo and in cell culture. In the adult brain, the catalytic subunits alpha1 and alpha2 are present in neurons throughout the brain. The AMPK-activating agent AICAR protected hippocampal neurons against death induced by glucose deprivation, chemical hypoxia, and exposure to glutamate and amyloid beta-peptide. Suppression of levels of the AMPK alpha1 and alpha2 subunits using antisense technology resulted in enhanced neuronal death following glucose deprivation, and abolished the neuroprotective effect of AICAR. Thus, given the role of AMPK activation in modifying neuronal survival under conditions of cellular stress, treatment with the composition to increase AMPK activity is useful in protecting neurons against metabolic and excitotoxic insults relevant to the pathogenesis of several different neurodegenerative conditions as would be recognized by one of skill in the art.

Example 18

Conditions and disorders associated with hypoxia are among those treatable by administering a composition comprising a compound that activates AMPK. AMPK is believed to play a role in regulating ketone body production by astrocytes. (J Neurochem, 73(4): 1674-82, 1999, herein incorporated by reference in its entirety). Incubation of astrocytes with AICAR has been shown to stimulate both ketogenesis from palmitate and carnitine palmitoyltransferase I concomitant to a decrease of intracellular malonyl-CoA levels and an inhibition of acetyl-CoA carboxylase/fatty acid synthesis and 3-hydroxy-3-methylglutaryl-CoA reductase/cholesterol synthesis. Moreover, microdialysis experiments have shown AICAR to stimulate brain ketogenesis markedly. Incubation of astrocytes with azide has been shown to lead to a remarkable drop of fatty acid beta-oxidation. However, activation of AMPK during hypoxia was shown to compensate the depression of beta-oxidation, thereby sustaining ketone body production. The effect is believed to rely on the following cascade: hypoxia=>increase of the AMP/ATP ratio=>AMPK stimulation=>acetyl-CoA carboxylase inhibition=>decrease of malonyl-CoA concentration=>carnitine palmitoyltransferase I deinhibition=>enhanced ketogenesis. Furthermore, incubation of neurons with azide has been shown to blunt lactate oxidation, but not 3-hydroxybutyrate oxidation. Thus, given the role of AMPK activation in regulating ketone body production by astrocytes, treatment with the composition to increase AMPK activity is useful in promoting astrocytes to produce ketone bodies as a substrate for neuronal oxidative metabolism during hypoxia Example 19

Conditions and disorders associated with diminished insulin sensitivity of muscle glucose transport are treatable by administering a composition comprising a compound that activates AMPK. A study to determine whether hypoxia and AICAR, which also activate AMPK and stimulate glucose transport, also induce an increase in insulin sensitivity has been reported. (Am J Physiol Endocrinol Metab, 282(1): E18-23, 2002, herein incorporated by reference in its entirety) The study found that the increase in glucose transport in response to 30 microU/ml insulin was about twofold greater in rat epitrochlearis muscles that had been made hypoxic or treated with AICAR 3.5 h previously than in untreated control muscles. This increase in insulin sensitivity was similar to that induced by a 2-h bout of swimming or 10 min of in vitro electrically stimulated contractions. Neither phosphatidylinositol 3-kinase activity nor protein kinase B (PKB) phosphorylation in response to 30 microU/ml insulin was enhanced by prior exercise or AICAR treatment that increased insulin sensitivity of glucose transport. Inhibition of protein synthesis by inclusion of cycloheximide in the incubation medium for 3.5 h after exercise did not prevent the increase in insulin sensitivity. Contractions, hypoxia, and treatment with AICAR all caused a two- to three-fold increase in AMPK activity over the resting level. These results provide evidence that the increase in insulin sensitivity of muscle glucose transport that follows exercise is mediated by activation of AMPK. Thus, treatment with the composition to increase AMPK activity is useful in increasing insulin sensitivity of muscle glucose transport.

Example 20

Occurrences of hepatic ischemia-reperfusion (I/R) injury associated with liver transplantation and hepatic resections can be reduced by administering a composition comprising a compound that activates AMPK. Preconditioning is known to preserve energy metabolism in liver during sustained ischemia. A study has been reported that investigates: 1) whether preconditioning induces AMPK activation; and 2) if AMPK activation leads to ATP preservation and reduced lactate accumulation during prolonged ischemia and its relationship with NO. (Hepatology, 34(6): 1164-73, 2001, herein incorporated by reference in its entirety) Preconditioning was reported to activate AMPK and concomitantly reduce ATP degradation, lactate accumulation, and hepatic injury. The administration of an AMPK activator, AICAR, before ischemia simulated the benefits of preconditioning on energy metabolism and hepatic injury. The inhibition of AMPK abolished the protective effects of preconditioning. The effect of AMPK on energy metabolism was independent of NO because the inhibition of NO synthesis in the preconditioned group and the administration of the NO donor before ischemia, or to the preconditioned group with previous inhibition of AMPK, had no effect on energy metabolism. Thus, given the role of AMPK activation in the protective effect against ischemia, treatment with the composition to increase AMPK activity is useful in surgical and pharmacologic strategies aimed at reducing hepatic I/R injury.

Example 21

Conditions and disorders associated with hyperglycemia are treatable by administering a composition comprising a compound that activates AMPK. It has recently been reported that therapeutic doses of metformin increase AMPK activity in vivo in subjects with type 2 diabetes. (Diabetes, 51(7): 2074-81, 2002, herein incorporated by reference in its entirety) Metformin treatment for 10 weeks significantly increased AMPK alpha2 activity in the skeletal muscle, and this was associated with increased phosphorylation of AMPK on Thr172 and decreased acetyl-CoA carboxylase-2 activity. The increase in AMPK alpha2 activity was likely due to a change in muscle energy status because ATP and phosphocreatine concentrations were lower after metformin treatment. Metformin-induced increases in AMPK activity were associated with higher rates of glucose disposal and muscle glycogen concentrations. These findings suggest that the metabolic effects of metformin in subjects with type 2 diabetes may be mediated by the activation of AMPK alpha2. Given the hypoglycemic effect imparted by the activation of AMPK, treatment with the composition to increase AMPK activity is useful to lower blood glucose concentrations by decreasing hepatic glucose production and increasing glucose disposal in skeletal muscle.

Example 22

Conditions and disorders associated with insulin resistance syndrome are treatable by administering a composition comprising a compound that activates AMPK. Insulin resistance syndrome is associated with obesity, type 2 diabetes, and muscle paralysis. (PCT/US01/19283, filed Jun. 14, 2001, and PCT/US01/18812, filed Jun. 11, 2001, both of which are herein incorporated by reference, each in its entirety.) Insulin resistance syndrome is also associated with several risk factors for cardiovascular disease. Chronic chemical activation of AMP-activated protein kinase by the adenosine analog AICAR has been shown to augment insulin action, upregulate mitochondrial enzymes in skeletal muscles, and decrease the content of intra-abdominal fat, including that ocurring in obesity. Furthermore, acute AICAR exposure has been found to reduce sterol and fatty acid synthesis in rat hepatocytes incubated in vitro as well as suppress endogenous glucose production in rats under euglycemic clamp conditions. A recent study investigated whether chronic AICAR administration, in addition to the beneficial effects on insulin sensitivity in type 2 diabetes, is capable of improving other phenotypes associated with the insulin resistance syndrome. (Diabetes, 51(7): 2199-206, 2002, herein incorporated by reference in its entirety) AICAR administration significantly reduced plasma triglyceride levels ($P<0.01$ for AICAR vs. AL, and $P=0.05$ for AICAR vs. PF) and free fatty acids ($P<0.01$ for AICAR vs. AL, and $P<0.05$ for AICAR vs. PF) and increased HDL cholesterol levels ($P<0.01$ for AICAR vs. AL and PF). AICAR treatment also lowered systolic blood pressure by 14.6+/−4.3 mmHg ($P<0.05$), and AICAR-treated animals exhibited a tendency toward decreased intra-abdominal fat content. Furthermore, AICAR administration normalized the oral glucose tolerance test and decreased fasting concentrations of glucose and insulin close to the level of the lean animals. Finally, in line with previous findings, AICAR treatment was also found to enhance GLUT4 protein expression and to increase maximally insulin-stimulated glucose transport in primarily white fast-twitch muscles. In view of the strong evidence that activating AMPK improves glucose tolerance, improves the lipid profile, and reduces systolic blood pressure, treatment with the composition to increase AMPK activity is useful to reduce metabolic disturbances and lowers blood pressure characteristic of insulin resistance syndrome.

While we have hereinbefore described a number of embodiments of this invention, it is apparent that our basic embodiments can be altered to provide other embodiments that utilize the products and processes of this invention. Therefore, it will be appreciated that the scope of this invention includes all alternative embodiments and variations which are defined in the foregoing specification and by the claims appended hereto; and the invention is not to be limited by the specific embodiments that have been presented herein by way of example.

We claim:

1. A method for activating adenosine 5'-monophosphate-activated protein kinase (AMPK) in a patient in need thereof, wherein the method comprises malting barley, grinding the malted barley, and extracting the malted barley with a solvent to obtain a malted barley extract; fractionating the malted barley extract by ion exchange chromatography to form fractions thereof; pooling the desired fractions and optionally removing protein from the pooled fractions by molecular sieving chromatography to prepare a low-molecular weight composition from a formed fraction; administering to said patient the low molecular weight composition in therapeutically effective amount that activates AMPK.

2. The method of claim 1, wherein the at least some of the fractions comprise a thaumatin-like protein.

3. The method of claim 2, wherein the low-molecular weight composition has an absorption maximum at about 260 nm.

4. The method of claim 1, wherein the patient suffers from obesity.

5. The method of claim 1, wherein the patient suffers from insulin resistance.

6. A method for treating a patient suffering from a condition or disorder associated with AMPK regulation, wherein the method comprises activating the AMPK according to a method of claim 1.

7. The method of claim 6, wherein the low-molecular weight composition has an absorption maximum at about 260 nm.

8. The method of claim 6, wherein the low-molecular weight composition is orally administered in 3 daily doses of 500 mg.

9. The method of claim 6, wherein the condition or disorder is obesity.

10. The method of claim 6, wherein the condition or disorder is insulin resistance.

11. A process for purifying from an extract of ground barley malt a composition comprising an agent that activates AMPK, wherein the process comprises:

(1) fractionating the extract of ground barley malt by ion exchange chromatography into protein fractions; (2) collecting one or more protein fractions; (3) removing a thaumatin-like protein from the one or more protein fractions by molecular sieving chromatography; and (4) pooling the fractions if more than one fraction is collected to result in a low-molecular weight composition that has an absorption maximum at about 260 nm.

12. A composition that comprises a agent that activates AMPK and that is produced by the process of claim 11.

* * * * *